United States Patent [19]

Bussard et al.

[11] 4,440,178
[45] Apr. 3, 1984

[54] IMPLANTABLE ELECTRODE

[75] Inventors: Adrien Bussard, Meierskappel, Switzerland; Fritz Aldinger, Rodenbach; Franz Sperner, Hanau, both of Fed. Rep. of Germany

[73] Assignees: Kontron AG, Zurich, Switzerland; W. C. Heraeus GmbH, Hanau, Fed. Rep. of Germany

[21] Appl. No.: 333,944

[22] Filed: Dec. 23, 1981

[30] Foreign Application Priority Data

Dec. 23, 1980 [CH] Switzerland ............... 9523/80

[51] Int. Cl.³ ............................................. A61N 1/04
[52] U.S. Cl. .................................. 128/784; 128/419 P
[58] Field of Search ............................ 128/784–786, 128/419 P

[56] References Cited

U.S. PATENT DOCUMENTS

| 535,466 | 1/1976 | Cannon | 128/419 P |
|---|---|---|---|
| 2,895,479 | 7/1959 | Lloyd | 128/639 |
| 3,476,116 | 11/1969 | Parsonnet et al. | 128/784 |
| 3,749,101 | 7/1973 | Williamson | 128/419 P |
| 3,890,977 | 6/1975 | Wilson | 128/419 P |
| 3,911,928 | 10/1975 | Lagergren | 128/419 P |
| 3,964,470 | 6/1976 | Trombley | 128/784 |
| 4,010,759 | 3/1977 | Boer | 128/419 P |
| 4,011,861 | 3/1977 | Enger | 128/419 P |
| 4,030,508 | 6/1977 | Thalen | 128/419 P |
| 4,033,357 | 7/1977 | Helland et al. | 128/785 |
| 4,156,429 | 5/1979 | Amundson | 128/419 P |
| 4,280,514 | 7/1981 | MacGregor | 128/786 |

FOREIGN PATENT DOCUMENTS

| 42551 | 12/1981 | European Pat. Off. | 128/419 P |
| 2056493 | 5/1972 | Fed. Rep. of Germany | 128/419 P |

OTHER PUBLICATIONS

Lewin et al., Trans. Amer. Soc. Artif. Int. Organs, vol. XIII, pp. 345–349 (1967).
Mindt et al., Medical and Biological Engineering, pp. 659–660 (Sep. 1973).
Schaldach et al., "Advances in Pacemaker Technology" Berlin/Heidelberg/New York, pp. 241–305 (1975).

*Primary Examiner*—Lee S. Cohen
*Attorney, Agent, or Firm*—Jon S. Saxe; Bernard S. Leon; George W. Johnston

[57] ABSTRACT

A porous electrode, particularly a cardiac pacemaker electrode is described which is implantable in organic tissue. The electrode has a sintered member made of electrically conductive particles. In a portion of the electrode surface the particles are covered wtih a material of lower electrical conductivity than that of the particles. Another portion of the surface is coated with a metal inert to body fluids. Suitable materials for the particles are metals or alloys from the group containing tantalum, titanium, mobium, zirconium as well as cobalt-chromium-based alloys.

13 Claims, 3 Drawing Figures

IMPLANTABLE ELECTRODE

BACKGROUND OF THE INVENTION

This invention relates to a porous electrode for implanation in organic tissue, more particularly a pacemaker electrode.

Porous electrodes for implanation is organic tissue, more particularly pacemaker electrodes, are known from U.S. Pat. No. 4,011,861. They consist of an electrically conductive part, the surface of which can come into contact with body fluids and is completely enclosed by an inert porous material, the pores of which have a diameter of from 0.5 to 1,000 μm. The electrically conductive part may be compact or porous. Platinum, iridium, niobium, indium, palladium, titanium, tantalum, vanadium, tungsten, chromium, cobalt, stainless steel, alloys of some of these metals, and carbon, are cited as materials for this part. The porous covering may be electrically conductive or electrically non-conductive. When it is electrically conductive it may consist of metal, carbon, a metal-coated non-conductor, an electrically conductive plastic, or the same material as the electrically conductive electrode part it encloses. If it is electrically non-conductive, it may consist of ceramics, aluminium oxide, silicon dioxide, calcium oxide, magnesium oxide, titanium oxide and/or zirconium oxide or a porous ceramic made from such oxides and available commercially under the name Cerosium. The electrodes described are constructed in the form of a spiral member.

U.S. Pat. No. 3,476,116 discloses a tubular electrode for pacemakers consisting of a two-stage housing of dielectric material, such as plastic, which contains a spiral of platinum iridium, the diameter of which is adapted to the diameter of the tube of the respective housing stage. The base of the housing is formed with a 1 mm² opening. The housing is filled with an electrically conductive solution, such as aqueous salt solution.

DETAILED DESCRIPTION OF THE INVENTION

The object of the invention is to provide an electrode which is adapted to be implanted in organic tissue and which has a low stimulus threshold, reaches the chronic stimulus threshold very rapidly, in addition has a minimum increase in stimulus threshold between the intra-operative and the maximum temporary stimulus threshold, and requires minimum stimulation.

In an electrode of the type referred to hereinbefore, to this end, according to the invention, it consists of a sintered member made from electrically conductive particles which are provided with a thin coating of a material having a lower electrical conductivity than the material of the particles, said coating being provided at least in the surface region of the electrode at the areas where the particles are not interconnected with each other, the material of the particles consists of a metal, a metal alloy, or a metal compound of an element of the group comprising tantalum, titanium, niobium and zirconium or of a cobalt-chromium-based alloy, and part of the surface of the sintered member is provided with a metal which is a good electrical conductor and which is inert to body fluids.

Platinum, iridium or platinum-iridium alloys having an iridium content of up to 20% by weight, remainder platinum, have proved particularly suitable at metal which is inert to body fluids and with which part of the surface of the sintered member is provided.

Good results have been obtained with electrodes in which the particles consist of tantalum. More particularly, a sintered member consisting of anodized tantalum has proved satisfactory.

Advantageously, the surface of the sintered member is partially provided with platinum, more particularly when tantalum is used as particle material or anodized tantalum.

The invention is not restricted to the above choice and combination of materials however.

For example, the particle material used may be electrically conductive $TiO_x$ ($x=0.25$ to 1.5). In the surface region of the electrode the particles are then provided by oxidation, with a thin electrically non-conductive $TiO_2$ coating at the areas where they have not sintered together.

The following are also examples of suitable particle materials: nitrides, carbides or carbonitrides of Ta, Ti, Nb or Zr; Ta-W alloys containing up to 10% by weight of W; Ti-Al-Fe alloys containing up to 6% by weight of Al and up to 2.5% by weight of Fe.

In electrodes according to the invention the pore size of the sintered material is advantageously so selected that most of the pores have a diameter open to the body tissue in the range from 10 to 50 μm.

Electrodes according to the invention surprisingly have a chronic stimulus threshold of about 0.3 V, which is comparable to the intra-operative threshold. In known pacemaker electrodes a chronic stimulus threshold of 2–3 V and an intra-operative threshold of 0.4 to 1 V have been measured under comparable conditions. In the electrodes according to the invention, therefore, the chronic stimulus threshold is about one order of magnitude lower. Equally favourable results were verified for the stimulation energy. For electrodes according to the invention it is about 0.15 to 0.2μ Joule, and is therefore about two orders of magnitude less than with conventional electrodes, the stimulation energy of which is about 15 to 20μ Joule.

In electrodes according to the invention the stimulation voltage is below the voltage at which body fluids decompose.

These advantageously low values give pacemakers with electrodes according to the invention a much longer life; the life is at least doubled for the same pacemaker battery capacity. Pacemakers with an electrode according to the invention require only one battery for operation, without doubling the voltage, whereas it was hitherto necessary either to use two series-connected batteries or one battery with voltage doubling.

These advantages of the invention are particularly apparent in electrodes of the kind which are cup-shaped and in which the cup consists of a sintered member made from tantalum anodized at least in the surface region, the inner walls and possibly the edge being provided with a thin platinum coating and most of the pores of the sintered member having a diameter in the range from 10 to 50μm.

The advantages of electrodes according to the invention as indicated above mean a considerable reduction in tissue irritation when used. The electrodes have full sensing sensitivity again within a few milliseconds after the stimulation pulse. They can readily be introduced, for example by subclavicular puncture using normal, i.e. standard-size, instruments, thus extensively avoiding vessel injuries of which there is a risk when over-size instruments are used.

Exemplified embodiments of electrodes according to the invention are shown in vertical section in the drawings wherein.

Figure 1:
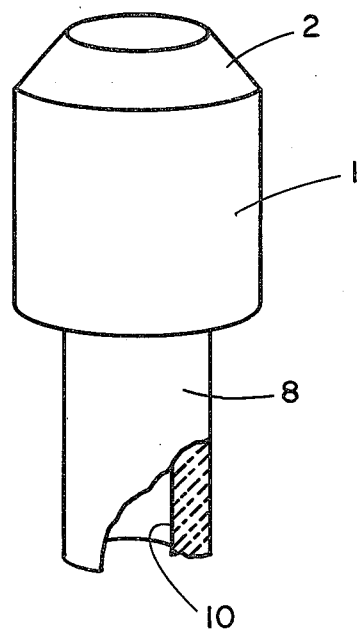
FIG. 1 shows a cylindrical electrode partly in cross-section

The electrode 1 shown in FIG. 1 consists of a porous sintered member made from tantalum which is anodized at the free surfaces, i.e., at those areas of the tantalum particles in the surface zone of the electrode where the particles are not interconnected. The sintered member has a platinum coating 2 near the tip of the electrode.

This electrode is produced by pressing of tantalum powder of a particle size ≦60 μm but ≦40 μm is a mould at a pressure of 2500 bar and then sintering the resulting pressing at a temperature of about 2200° C. for a period of about 1 to 3 hours. After cleaning and activation by conventional techniques the sintered member is anodized in dilute phosphoric acid, to form a thin Ta-oxide coating on the free surface of the Ta particles, i.e., at those areas of the particles of the surface zone of the electrode which have not sintered together. In order to apply the platinum coating to part of the surface of the sintered member, this part is polished to remove the Ta-oxide coating and then platinum is deposited galvanically from a commerical platinum bath.

Figure 2:
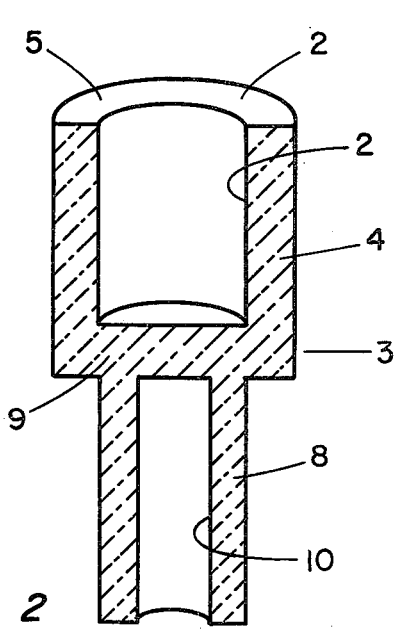
FIG. 2 shows a cross-section a cup-shaped electrode.

FIG. 2 shows a cup-shaped electrode. The cup consists of a porous sintered member 3 made from anodized tantalum. The wall 4 and possibly the base 9 have platinum coatings 2 on the inside. It has been found advantageous to provide a platinum coating 2 on the edge 5 of the cup as well.

The cup-shaped electrode is produced by making a cup-shaped pressing from Ta-powder of a particle size ≦60 μm but ≧40 μm the pressure used being 2500 bar. This pressing is sintered at a temperature of 2200° C. for a period of from 1 to 3 hours and after cleaning and activation is then anodized in dilute phosphoric acid. The inner wall of the cup is polished, as is also the edge of the cup if necessary, whereupon platinum is galvanically deposited on the polished surfaces from a commercial platinum bath.

Figure 3:
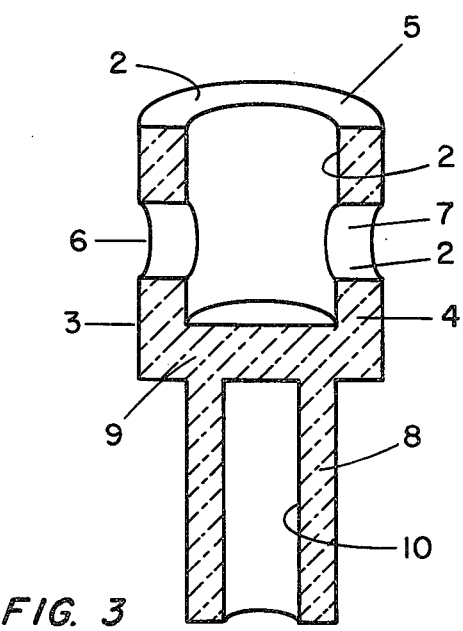
FIG. 3 shows a cross-section a cup-shaped electrode with passages in the wall of the cup.

The electrode shown in FIG. 3 differs basically from that shown in FIG. 2 in that the wall 4 has passages 6. The passage walls 7 may also be provided with a platinum coating 2. The passages are formed in the wall by cemented-carbide drills. Otherwise the production of this cup-shaped electrode is identical to that described in connection with FIG. 2. The passages are drilled in the wall of the sintered member before it is anodized. In all the examples illustrated, the power supply is via the cnnection 8 at the back, the inner surface of the connection 8—which consists of anodized tantalum—being either just polished or also coated galvanically with the platinum coating 10 after polishing.

We claim:

1. A porous electrode for implanting in organic tissue, comprising a sintered member of electrically conductive particles, said member having
   (i) a first surface portion of said sintered particles which is anodized at least at the non-interconnected area of the particles so as to form a relatively thin metal oxide coating on said surface portion and
   (ii) a second surface portion coated with an electrically conductive metal inert to body fluids, said two surface portions being configured and adapted for intimate contact with the tissue.

2. The electrode of claim 1 wherein the electrode is configured as a pacemaker electrode.

3. The electrode of claim 2 wherein the particles are tantalum, titanium, niobium, zirconium or a cobalt-chromium-based alloy.

4. The electrode of claim 3 wherein the particles are tantalum.

5. The electrode of claim 4 wherein the coating is anodized tantalum.

6. The electrode of claim 5 wherein said electrically conductive metal inert to body fluids is platinum.

7. The electrode of claim 6 wherein at least the first surface portion of the sintered member has pores of a diameter between about 10 and about 50 μm.

8. The electrode of claim 2 wherein said electrically conductive metal inert to body fluids is platinum, iridium or a platinum-iridium alloy having an iridium content of about 0 to about 20% by weight.

9. The electrode of claim 2 wherein the electrode is configured and and dimensioned in the shape of a cup having an inner wall, an outer wall and a base member, said base member configured for connection to an electrical power source.

10. The electrode of claim 8 wherein the inner wall of the cup shape electrode is coated with said electrically conductive metal inert to body fluids.

11. The electrode of claim 10 wherein the cup shape electrode defines at least one passage through the outer and inner wall.

12. The electrode of claim 11 wherein said passage has on its surface said electrically conductive metal inert to body fluids.

13. A porous pacemaker electrode for implanting in organic tissue comprising a sintered member made of electrically conductive sintered tantalum particles and having a surface area with pores of a diameter between about 10 and about 50 μm, said surface area having a first surface portion of anodized tantalum and a second surface portion of platinum for enhancing electrical contact with the tissue for stimulation thereof, said sintered member configured and dimensioned as a cup having an inner wall of anodized tantalum, an outer wall and a base member for effecting contacting with an electric power supply.

* * * * *